United States Patent [19]

Avar

[11] Patent Number: 4,695,600

[45] Date of Patent: Sep. 22, 1987

[54] TETRAALKYLPIPERIDINES

[75] Inventor: Lajos Avar, Biel-Benken, Switzerland

[73] Assignee: Sandoz Ltd., Basel, Switzerland

[21] Appl. No.: 875,130

[22] Filed: Jun. 17, 1986

[30] Foreign Application Priority Data

Jun. 20, 1985 [GB] United Kingdom ............... 8515672

[51] Int. Cl.⁴ ................ C07D 417/12; C07D 417/14; C08K 5/34
[52] U.S. Cl. ..................................... 524/103; 546/16; 546/186; 546/187; 546/188; 546/189; 546/190; 546/191; 546/209; 546/244; 524/83; 524/99
[58] Field of Search ............... 546/16, 186, 187, 188, 546/189, 190, 191, 209, 244; 524/83, 99, 102, 103

[56] References Cited

U.S. PATENT DOCUMENTS 4,088,629  5/1978  Uhrhan et al. ................ 546/16
4,089,841  5/1978  Lantzsch et al. ............. 546/209

Primary Examiner—Robert T. Bond
Attorney, Agent, or Firm—Gerald D. Sharkin; Richard E. Vila; Thomas C. Doyle

[57] ABSTRACT

These compounds are useful as light stabilizers in polymeric systems.

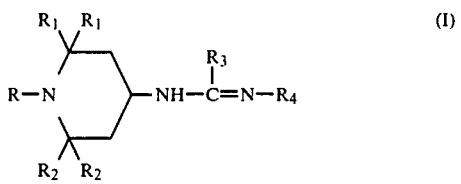

in which $R_1$, $R_2$, $R_3$ and $R_4$ are organic radicals.

14 Claims, No Drawings

TETRAALKYLPIPERIDINES

The invention relates to novel tetraalkylpiperidine compounds which are useful as light stabilisers for example in lacquer systems.

According to the invention there is provided a compound of formula I

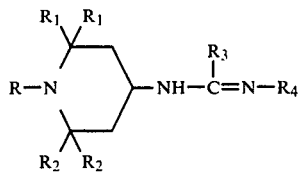

in which R is hydrogen, unsubstituted $C_{1-18}$alkyl, unsubstituted $C_{1-21}$alkylcarbonyl, unsubstituted $C_{2-19}$alkenylcarbonyl, $C_{1-21}$alkoxycarbonyl, phenylcarbonyl, phenyl$C_{1-4}$alkylcarbonyl, $C_{1-4}$alkylphenylcarbonyl, oxygen or

where
R$_6$ is

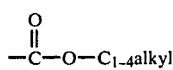

or —NR$_7$R$_8$; R$_7$ being hydrogen, $C_{1-12}$alkyl, $C_{5-6}$cycloalkyl, phenyl or $C_{1-12}$alkyl-phenyl and R$_8$ is hydrogen or $C_{1-12}$alkyl;

R$_1$ is —CH$_2$—C$_{1-4}$alkyl or —CH$_3$ or both R$_1$s together form —CH$_2$)$_5$;

R$_2$ is —CH$_2$—C$_{1-4}$alkyl or —CH$_3$ or both R$_2$s together form —CH$_2$)$_5$;

R$_3$ is unsubstituted $C_{1-18}$alkyl, phenyl, unsubstituted or substituted by 1, 2 or 3 groups selected from $C_{1-18}$alkyl, $C_{1-4}$alkoxy and halogen; or is a group (a)

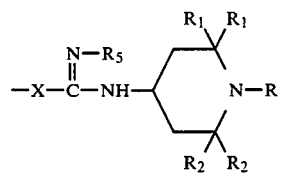

R$_4$ is $C_{1-18}$alkyl; phenyl, unsubstituted or substituted by 1 to 3 groups selected from $C_{1-18}$alkyl, $C_{1-4}$alkoxy and halogen or is a group (b) or (c)

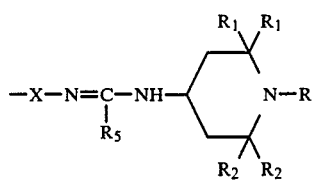

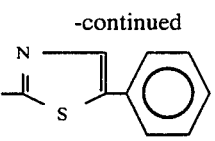

where X is a direct bond or a bridging group and R$_5$ is unsubstituted $C_{1-18}$alkyl or phenyl unsubstituted or substituted by 1 to 3 groups selected from $C_{1-18}$alkyl, $C_{1-4}$alkoxy and halogen;

with the proviso that when R$_3$ is a group (a) R$_4$ is not a group (b).

In this Specification where a significance appears more than once in a formula its significances are independent of one another unless indicated to the contrary. All alkyl group (containing more than 2 carbon atoms) and all alkenyl groups (containing more than 2 carbon atoms) are linear or branched. Preferably any halogen is chloro or bromo.

Preferably in R, $C_{1-21}$alkylcarbonyl is $C_{1-12}$alkylcarbonyl, more preferably $C_{1-4}$alkylcarbonyl.

Preferably in R, $C_{2-19}$alkenylcarbonyl is $C_{2-12}$alkenylcarbonyl, more preferably $C_{2-4}$alkenylcarbonyl.

Preferably R is R$_a$ where R$_a$ is hydrogen, $C_{1-6}$alkyl, acetyl, propionyl or

(where R$_{6a}$ is

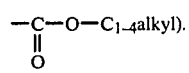

More preferably R is R$_b$ where R$_b$ is hydrogen, $C_{1-4}$alkyl or acetyl. Most preferably R is R$_c$ where R$_c$ is hydrogen, methyl or acetyl of which hydrogen and acetyl are preferred, especially hydrogen.

Preferably R$_1$ and R$_2$ are all —CH$_3$.

Preferably R$_3$ is R$_{3a}$ where R$_{3a}$ is phenyl, unsubstituted or substituted by $C_{1-6}$alkyl, $C_{1-4}$alkoxy or chloro or is a group of formula a$_1$

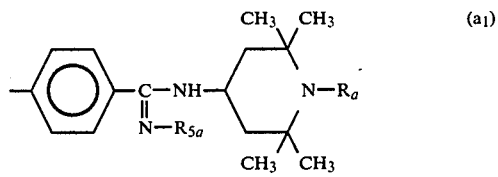

where R$_{5a}$ is defined below.

X is preferably X' where X' is phenylene, diphenylene methane, 4,4'-diphenylene or 4,4'-diphenylene oxide, more preferably X" where X" is 1,4-phenylene or 4,4'-diphenylene.

Preferably R$_4$ is R$_{4a}$ where R$_{4a}$ is $C_{4-18}$alkyl, phenyl, unsubstituted or substituted by one $C_{1-4}$alkyl, $C_{1-4}$alkoxy or chlorine or is a group of formula b$_1$

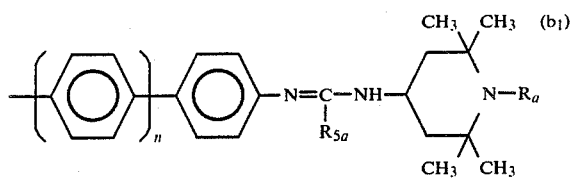

where
n is 0 or 1; and
$R_{5a}$ is $C_{1-18}$alkyl or phenyl unsubstituted or substituted by one $C_{1-4}$alkyl group.

The compounds of formula I can be made from known compounds by known methods for example by reacting 1 mole of a compound of formula II

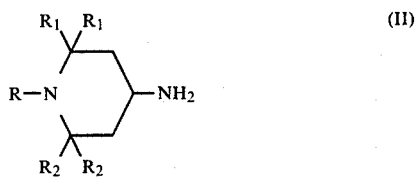

with one mole of a compound of formula III

Compounds of formula II or III are known or can be made from known compounds by known methods. Preferably the reaction takes place in an inert solvent such as tetrahydrofurane, benzene, toluene or methylene chloride. Preferably the temperature of the reaction is from 0° to 4° C. Cooling may be necessary at times to keep the temperatures below 40° C.

Further, according to the invention there is provided a polymeric composition comprising a polymeric material and a compound of formula I.

The concentration of compound of formula I employed in the polymeric material is suitably 0.01 to 5% by weight, preferably 0.02 to 1% by weight. The compound may be added before, during or after the polymerization step, and may be added in solid form; in solution, preferably as a liquid concentrate containing from 20 to 80% by weight of compound of formula I; or as a solid masterbatch composition containing 20 to 80% by weight of compound of formula I and 80 to 20% by weight of a solid polymeric material which is identical with or compatible with the polymeric material to be stabilized.

Still further according to the invention there is provided a process for stabilising a polymeric substrate comprising adding to the substrate a compound of formula I defined above.

Compounds of formula I are useful as stabilizers to protect polymeric materials against degradation by light. The compounds have particularly good solubility and miscibility in solvent systems and in liquid polymers and prepolymers, which makes them useable in a wide range of polymeric materials.

Suitable polymeric materials include plastic materials for example polyethylene, polypropylene, ethylene/propylene copolymers, polyvinyl chloride, polyester; polyamide, polyurethane, polyacrylonitrile, ABS, terpolymers of acrylates, styrene and acrylonitrile, styrene/acrylonitrile and styrene/butadiene. Other plastics materials such as polybutylene, polystyrene, chlorinated polyethylene, polycarbonate, polymethylmethacrylate, polyphenylene oxide, polypropylene oxide, polyacetals, phenol/formaldehyde resins and epoxy resins may also be used. Preferred plastic materials are polypropylene, polyethylene, ethylene/propylene copolymers and ABS. Natural polymers for example natural rubber may also be stabilized, as may lubricating oils containing polymeric material.

The compounds of formula I may be incorporated by known methods into the polymeric material to be stabilized. Of particular importance is blending of the compounds with thermoplastic polymers in the melt, for example in a melt blender or during the formation of shaped articles, including foils, films, tubes, containers, bottles, fibres and foams by extrusion, injection moulding, blow moulding, spinning or wire coating.

It is not essential for the polymeric material to be fully polymerised before mixing with the compounds according to the invention. The compounds may be mixed with monomer, prepolymer or precondensate, and the polymerisation or condensation reaction carried out subsequently. This will of course be the preferred method of incorporation of the compounds into thermosetting polymers, which cannot be melt blended.

The compounds of formula I may be used alone or in combination with other stabilizers, for example antioxidants. Examples of other stabilisers include sterically hindered phenols, sulphur or phosphorus-containing compounds or mixtures of these. More specific examples of these other stabilisers are benzofuran-2-ones; indolin-2-ones and sterically hindered phenols such as β-(4-hydroxy-3,5-ditert.-butylphenyl)propionyl stearate, methane tetrakis-(methylene-3(3',5'-ditert.-butyl-4-hydroxyphenyl-]-propionate], 1,3,3-tris-(2-methyl-4-hydroxy-5-tert.-butylphenyl)-butane, 1,3,5-tris(4-tert.-butyl-3-hydroxy-2,6-dimethylbenzyl)-1,3,5-triazin-2,4,6 (1H, 3H, 5H)-trione, bis(4-tert.-butyl-3-hydroxy-2,6-dimethylbenzyl)dithioterephthalate, tris(3,5-ditert.-butyl-4-hydroxybenzyl)isocyanurate, the triester of β-(4-hydroxy-3,5-ditert.-butylphenyl)propionic acid with 1,3,4-tris-(2-hydroxyethyl)-5-triazin-2,4,6 (1H, 3H, 5H)trione, bis[3,3-bis-(4'-hydroxy-3-tert.-butylphenyl)-butyric acid]glycol ester, 1,3,5-trimethyl-2,4,6 tris-(3,5-ditert.-butyl-4-hydroxy-benzyl)benzene, 2,2'-methylene-bis-(4-methyl-6-tert.-butylphenyl)terephthalate, 4,4-methylene-bis-(2,6-ditert.-butylphenol), 4,4'-butylidene-bis-(tert.-butyl-metacresol), 2,2'-methylene-bis-(4-methyl-6-tert.-butyl-phenol.

Sulphur-containing antioxidative co-stabilizers which may be used include for example distearylthiodipropionate, dilaurylthiodipropionate, methane tetrakis(-methylene-3-hexylthiopropionate), methane tetrakis(-methylene-3-dodecylthiopropionate) and dioctadecyl-disulphide. Phosphorus-containing co-stabilizers include for example trinonylphenyl phosphite, 4,9-distearyl-3,5,8,10-tetraoxadiphosphaspiroundecane, tris(2,4-ditert.-butylphenyl)phosphite and tetrakis(2,3-ditert.-butylphenyl)-4,4'-biphenylylene diphosphonite. Further additives such as aminoaryl compounds and U.V.-absorbers and light stabilizers e.g. 2-(2'-hydroxyphenyl)-benzotriazole, 2-hydroxybenzophenone, 1,3-bis-(2'-hydroxybenzoyl)benzene, salicylates, cinnamates, benzoates and substituted benzoates, sterically hindered amines and oxalic acid diamides may be used. Other known types of additives, e.g. flame retardants and antistatic agents, may also be added.

The compounds of the invention can also be used in photopolymeric substrates containing photoinitiators for the photopolymerisation.

The compounds of formula I are especially suitable for use in organic polymer-containing coatings, particularly automotive finishes.

Automotive finishes are generally solutions or dispersions of organic polymers or polymer precursors in organic solvents. The majority are stoving finishes, which require the application of heat, generally above 80° C., in order to harden the finish in an acceptable time once it has been applied to the primer-coated metal surface. The hardening step may be accelerated by the use of an acid catalyst. The effect of this heating may be to accelerate the chemical reaction between polymer precursors in a thermosetting system, or to bring about fusion of particles of a thermoplastic polymer.

Many automotive finishes are metallic finishes, which contain flakes of metal, usually aluminium, in order to provide optical effects due to reflection. Such finishes are often two-coat finishes, in which a clear top coat finish is applied over a base coat finish containing a single pigment or metal flakes. The compounds of formula I can be in the top coat finish or the ground coat finish, preferably the former. Such two-coat metallic finishes have particular need of U.V.-stabilizers in the top coat, since the polymer in this coat is not protected by light-absorbing pigments, and it is subjected to almost double the normal amount of radiation because of reflection of light from the lower metallic layer.

The compounds of formula I are suitable for use as U.V.-stabilizers in a wide range of liquid finishes, for example those based on combinations of melamine-formaldehyde resins with oil-modified polyester resins, polyacrylate resins with added crosslinkers, or saturated polyesters; or on self-crosslinkers, or saturated polyesters; or on self-crosslinked polyacrylate or polyacrylate resin co-polymerised with styrene.

Further examples are two-component finishes based on an aliphatic or aromatic di-isocyanate and a hydroxy-group-containing polyacrylate, polyester or polyether resin. These polyurethane 2 component finishes are preferably hardened at 60° to 120° C. Thermoplastic polyacrylate resins may also be used, the latter being particularly useful in metallic finishes, as are also polyacrylate resins with added crosslinkers in combination with melamine-formaldehyde resins etherified with butanol and, further, hydroxy-group-containing polyacrylate resins hardened with aliphatic di-isocyanates. In these cases it is preferred to use compounds of formula I in which R is alkyl or acyl.

The compounds of formula I are particularly useful in acid catalysed stoving finishes particularly in the top coat of two layer metallic finishes.

The compounds of formula I may be added to the finish at any stage in its manufacture, and may be added in solid form or in solution, preferably in the form of a liquid concentrate in a suitable solvent.

In practice the compounds of formula I are added to a finish as a solution in organic solvent (as a liquid finish) in which the binder material is between 35% (low solid finishes) and 70% by weight (high solid finishes). The binder material of the finish can be in aqueous or suspension form (as an aqueous finish) in which the binder material part makes up 20 to 30% by weight. However, the compounds of formula I can be added to known powder finishes.

The compounds of formula I are to be added to the liquid or powder finishes before stoving or hardening. Preferably the compounds of formula I are used in liquid finishes since it is easy to add exact dosages. It is particularly preferred to use a concentrate (preferably in a hydrocarbon solvent) containing at least 40% preferably 60 to 80% by weight of the total weight of the concentrate of a compound of formula I to introduce the compound of formula I to finishes for stoving.

The addition of from 0.01 to 5% by weight, preferably 0.2 to 2% by weight of one or more compounds of formula I gives a clear improvement in the light- and weather-stability of organic pigments in stoving finishes as well as reducing the tendency to hairline cracking and loss of gloss as the result of weathering. This is also found for metallic finishes and excellent long-term stability of the clear top coat of two layer metallic finishes is obtained. In such finishes, the compound of formula I may be added to the metallic undercoat, the clear top coat or both, preferably only to the clear top coat. The metal surface to be finished may be under-coated with primer coatings as is customary in the art of coating metal surfaces.

The invention will be illustrated by the following Examples in which all parts and percentages are by weight and all temperatures are in °C.

EXAMPLE 1

25.1 g (0.1 moles) of $C_6H_5C(Cl)=N-C_8H_{17}(n)$ in 70 ml of methylene chloride are added at 20° over 30 minutes to 15.6 g (0.1 moles) of 2,2,6,6-tetramethyl-4-aminopiperidine. A white mass results and the temperatures rises to 35° C. After 3 hours a 5% sodium bicarbonate solution is added. The mixture is then stirred a further 3 hours. The organic phase is separated off and the methylene chloride is distilled off. A clear brilliant yellow oil of the formula 1a

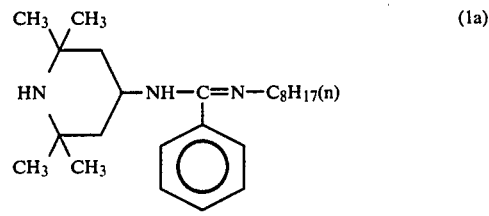

results.

EXAMPLES 2 TO 13

Compounds of the formula

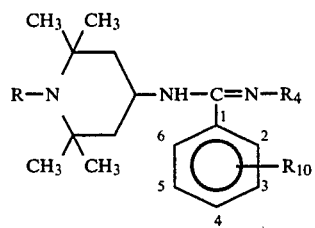

in which R, $R_4$ and $R_{10}$ are defined in the Table below, can be made from appropriate reactants by a method analogous to that of Example 1.

TABLE

| Ex. No. | R | R₄ | R₁₀ | position of R₁₀ |
|---|---|---|---|---|
| 2 | H | —C$_8$H$_{17}$(i) | —H | — |
| 3 | H | —C$_{12}$H$_{25}$(n) | —H | — |
| 4 | H | —C$_{18}$H$_{37}$(n) | —H | — |
| 5 | H | —C$_4$H$_9$(n) | —C$_4$H$_9$(n) | 4- |
| 6 | H | —C$_{12}$H$_{25}$(n) | —C$_4$H$_9$(n) | 4- |
| 7 | H | —C$_6$H$_5$ | —C$_4$H$_9$(n) | 4- |
| 8 | H | (phenyl with OC$_2$H$_5$) | —C$_4$H$_9$(n) | 4- |
| 9 | CH$_3$C(=O)— | (phenyl with Cl) | H | — |
| 10 | —CH$_3$ | C(CH$_3$)$_3$ | —Cl | 2-(phenyl) |
| 11 | nC$_6$H$_{13}$ | —nC$_4$H$_9$ | t-butyl | 4- |
| 12 | C$_2$H$_5$OC(=O)—C(=O)— | —(C$_6$H$_4$)—CH$_3$ | —OC$_2$H$_5$ | 4- |
| 13 | C$_2$H$_5$—C(=O)— | n-C$_6$H$_{13}$ | —OCH$_3$ | 2- |

EXAMPLES 14 AND 15

The following compounds can be formed by a method analogous to that of Example 1 by reacting 2 moles of

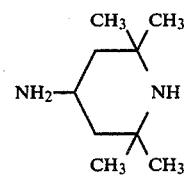

with 1 mole of

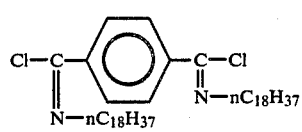

in Example 14 or 1 mole of

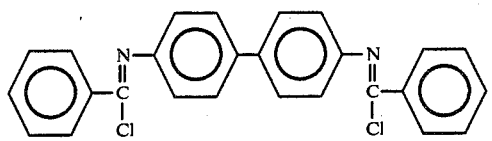

in Example 15.

EXAMPLE 14

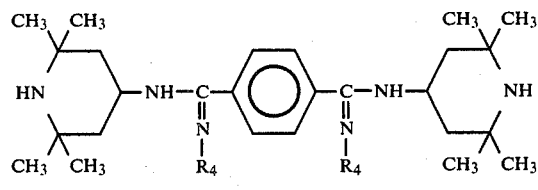

where R$_4$=nC$_{18}$H$_{37}$.

EXAMPLE 15

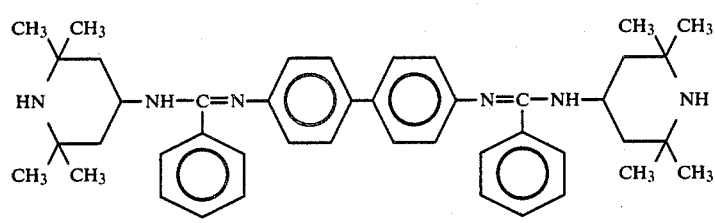

EXAMPLE 16

29.85 g of the compound of formula 16a

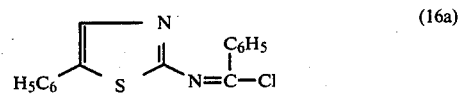           (16a)

and 22.7 g of the compound of formula 16b

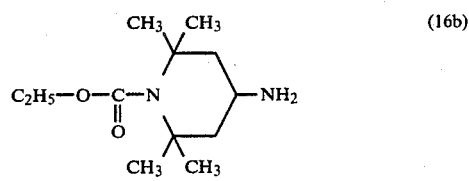           (16b)

in 70 parts of methylene chloride are reacted by a method analogous to that of Example 1. The resulting compound is of formula 16(c)

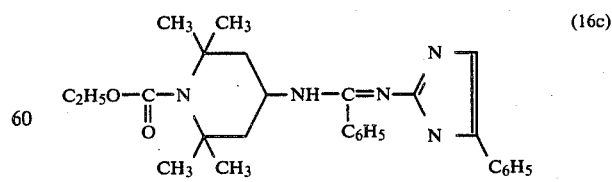           (16c)

APPLICATION EXAMPLE A

A clear finish of
80 Parts of Viacryl SC 344 (a 50% solution of an acryl resin from Vianova), 13.9 Parts of Maprenal MF 80 (a 72% solution of a melamine resin from Hoechst) and
4.1 Parts of Byketol OK (from Byk-Malinckrodt)
is added to 2 parts of a compound of formula 1a (described in Example 1). After 1 minute the light stabiliser material so formed is dissolved in a finish. The finish is applied conventionally (according to the known 2 layer procedure) to a metallic or single pigment finish whilst still wet by spraying to form a layer having a thickness of 30 to 40 μm. The resulting coating is then hardened at 140° C. for 30 minutes. The coating shows very good resistance to U.V. light and weathering.

APPLICATION EXAMPLE B

A clear finish of
29.5 Parts of Setalux C-1502 XX-60 (a 60% solution of an acryl resin from Synthese B.V.),
39.2 Parts of Setalux C-1382 BX-45 (a 45% solution of an acryl resin from Synthese B.V.),
21.4 Parts of Setamine US-138 BB-70 (a 70% solution of a melamine resin from Synthese B.V.),
2.5 Parts of Baysilonoil [(2% solution in Xylene) from Bayer] and
7.4 Parts of Depanol Y (a solvent from Hoechst)
is stirred together with 2.5 parts of a compound of formula 1a (described in Example 1) and 2 parts of an acid catalyst derived from phosphoric acid (Type: Catalyst 296-9 from American Cyanamid) to form a homogeneous mixture. The finish is applied conventionally (according to the known 2 layer procedure) to a metallic or single pigment finish whilst both are still wet by spraying to form a layer having a thickness of 30 to 40 μm. The resulting coating is then hardened at 110° C. for 20 minutes. The coating shows very good resistance to U.V. light and weathering.

APPLICATION EXAMPLE C

A clear finish of
75 Parts Macrynal SH 510 N (a hydroxy containing acryl resin from Bayer)
2 Parts of Baysilon-oil A [(1% solution in xylene) from Bayer]
0.3 Parts of dibutyl zinc dilaurate
0.35 Parts diethanolamine
5.0 Parts of ethylglycol acetate
5.0 Parts of Solvesso 100
6.0 Parts of Xylene and
6.35 Parts of butyl acetate
is added to 23.5 parts of a compound of formula 1a (described in Example 1) and 30 parts of Desmodur N 75 (from Bayer). The homogeneous mixture so formed is applied conventionally (according to the known 2 layer procedure) to a metallic or single pigment finish whilst both are still wet by spraying to form a layer having a thickness of 30 to 40 μm and the resulting coating is hardened over 20 minutes at 80° to 90° C. The resulting 2K-PUR coating shows a good resistance to U.V. light and weathering.

APPLICATION EXAMPLE D

A single white pigmented finish of
14.30 Parts of Setamine US-132 BB 70 (a 70% solution of a melamine resin from Synthese)
57.15 Parts of Setal 84 W-70 (a 70% solution of an alkyd resin from Synthese)
7.70 Parts of n-butanol
1.85 Parts of butylglycol acetate
9.50 Parts of Xylene and 25 Parts of titanium dioxide (Rutil type)
is added with 1.38 parts of the product of formula 1a (see Example 1). The finish is conventionally applied to a grounded steel metal to which a filler of layer thickness 20 to 30 μm has been annealed, by spraying and after standing for 30 minutes at room temperature the steel metal surface is annealed at 120° C. for 30 minutes. The resulting coating shows very good resistance to U.V. light and weathering.

In Application Examples A to D instead of the product of Example 1 the product of any one of the other Examples 2 to 16 can be used.

What is claimed is:
1. A compound of formula I

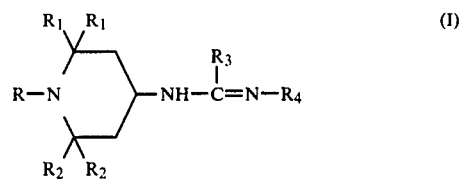

in which R is hydrogen, unsubstituted $C_{1-18}$alkyl, unsubstituted $C_{1-21}$alkylcarbonyl, unsubstituted $C_{2-19}$alkenylcarbonyl, $C_{1-21}$alkoxycarbonyl, phenylcarbonyl, phenyl$C_{1-4}$alkylcarbonyl, $C_{1-4}$alkylphenylcarbonyl, oxygen or

where
$R_6$ is

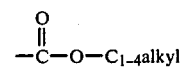

or $-NR_7R_8$; $R_7$ being hydrogen, $C_{1-12}$alkyl, $C_{5-6}$cycloalkyl, phenyl or $C_{1-12}$alkyl-phenyl and $R_8$ is hydrogen or $C_{1-12}$alkyl;
$R_1$ is $-CH_2-C_{1-4}$alkyl or $-CH_3$ or both $R_1$s together form $-(CH_2)_5-$;
$R_2$ is $-CH_2-C_{1-4}$alkyl or $-CH_3$ or both $R_2$s together form $-(CH_2)_5-$;
$R_3$ is unsubstituted $C_{1-18}$alkyl; phenyl, unsubstituted or substituted by 1, 2 or 3 groups selected from $C_{1-18}$alkyl, $C_{1-4}$alkoxy and halogen; or is a group (a)

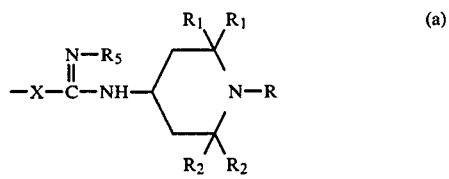

$R_4$ is $C_{1-18}$alkyl; phenyl, unsubstituted or substituted by 1 to 3 groups selected from $C_{1-18}$alkyl, $C_{1-4}$alkoxy and halogen; or is a group (b) or (c)

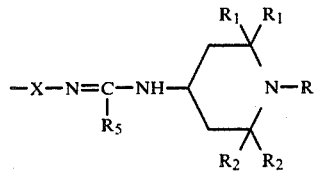

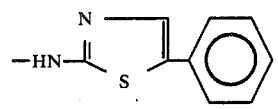

where X is a direct bond or a bridging group and $R_5$ is unsubstituted $C_{1-18}$alkyl or phenyl unsubstituted or substituted by 1 to 3 groups selected from $C_{1-18}$alkyl, $C_{1-4}$alkoxy and halogen;

with the proviso that when $R_3$ is a group (a) $R_4$ is not a group (b).

2. A compound according to claim 1 in which R is $R_a$ where $R_a$ is hydrogen, $C_{1-6}$alkyl, acetyl, propionyl or

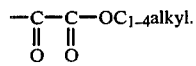

3. A compound according to claim 1, in which all groups $R_1$ and all groups $R_2$ are methyl.

4. A compound according to claim 1, in which $R_3$ is $R_{3a}$ where $R_{3a}$ is phenyl, unsubstituted or substituted by $C_{1-4}$alkyl, $C_{1-4}$alkoxy or halogen or is a group of formula $a_1$

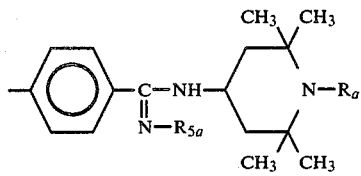

where
$R_a$ is hydrogen, $C_{1-6}$alkyl, acetyl, propionyl or

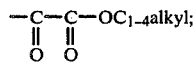

and
$R_{5a}$ is $C_{1-18}$alkyl or phenyl, unsubstituted or substituted by one $C_{1-4}$alkyl.

5. A compound according to claim 1, in which $R_4$ is $R_{4a}$ where $R_{4a}$ is $C_{4-18}$alkyl, phenyl, unsubstituted or substituted by one $C_{1-4}$alkyl, $C_{1-4}$alkoxy or chlorine or is a group of formula $b_1$

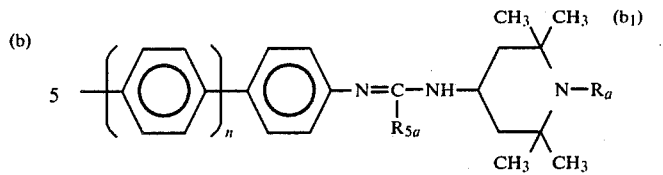

where
n is 0 or 1;
$R_a$ is hydrogen, $C_{1-6}$alkyl, acetyl, propionyl or

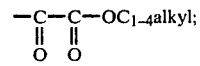

and
$R_{5a}$ is $C_{1-18}$alkyl or phenyl, unsubstituted or substituted by one $C_{1-4}$alkyl.

6. A polymeric composition comprising a polymeric material and a compound of formula I according to claim 1.

7. A composition according to claim 6, in which the amount of compound of formula I present is 0.01 to 5% by weight of polymeric material present.

8. A composition according to claim 6 in which the amount of compound of formula I present is 0.02 to 1% by weight of polymeric material present.

9. A composition according to claim 6 comprising one or more additives selected from antioxidants, flame retardants and antistatic agents.

10. A composition according to claim 6 comprising a compound of formula I according to claim 1 and a liquid finish based on combinations of melamine-formaldehyde resins with oil modified polyester resins, polyacrylate resins with added crosslinkers, or saturated polyesters or on self crosslinkers, or saturated polyesters; or on self crosslinked polyacrylate or polyacrylate resin copolymerised with styrene.

11. A polymeric coating comprising 0.01 to 5% by weight of a compound of formula I according to claim 1.

12. A stoved metallic coating according to claim 11.

13. A process for stabilising a polymeric substrate comprising adding to the substrate a stabilising amount of a compound of formula I according to claim 1.

14. A compound according to claim 5 wherein
R is $R_a$ where $R_a$ is hydrogen, $C_{1-6}$alkyl, propionyl or

$R_1$ and $R_2$ are all methyl and
$R_3$ is phenyl, unsubstituted or substituted by $C_{1-4}$alkyl, $C_{1-4}$alkoxy or halogen or is a group of formula $a_1$

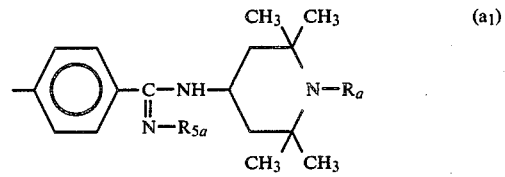

where
$R_{5a}$ is $C_{1-4}$alkyl or phenyl, unsubstituted or substituted by one $C_{1-4}$alkyl.

* * * * *